(12) United States Patent
Gwen

(10) Patent No.: US 6,973,933 B2
(45) Date of Patent: Dec. 13, 2005

(54) FLOSSER APPARATUS WITH DETACHABLE AND POSITIONABLE FLOSS ELEMENT

(76) Inventor: Patrick Gwen, 1815 Edmundson, Houston, TX (US) 77003

( * ) Notice: Subject to any disclaimer, the term of this patent is extended or adjusted under 35 U.S.C. 154(b) by 0 days.

(21) Appl. No.: 10/698,006

(22) Filed: Oct. 30, 2003

(65) Prior Publication Data

US 2005/0092346 A1 May 5, 2005

(51) Int. Cl.[7] .............................................. A61C 15/00
(52) U.S. Cl. ........................................................ 132/323
(58) Field of Search .................................. 132/323–327

(56) References Cited

U.S. PATENT DOCUMENTS

| | | | | |
|---|---|---|---|---|
| 1,438,939 A | * | 12/1922 | Ball | ............................ 132/324 |
| 2,187,899 A | | 1/1940 | Henny | |
| 2,233,936 A | * | 3/1941 | Campbell | .................... 132/325 |
| 2,517,806 A | * | 8/1950 | Streiler | ........................ 132/309 |
| 2,648,341 A | | 8/1953 | Moll | |
| 3,892,249 A | * | 7/1975 | Jones et al. | .................. 132/323 |
| 3,927,686 A | * | 12/1975 | Zambito | ...................... 132/323 |
| 4,051,857 A | * | 10/1977 | Zambito | ...................... 132/323 |
| 4,280,518 A | | 7/1981 | Gambaro | |
| D276,088 S | | 10/1984 | Fong | |
| 4,522,216 A | | 6/1985 | Bunker | |
| 4,832,062 A | * | 5/1989 | Grollimund et al. | ........ 132/327 |
| 5,010,906 A | * | 4/1991 | Preciutti | ...................... 132/323 |
| 5,016,660 A | | 5/1991 | Boggs | |
| 5,056,540 A | * | 10/1991 | Page | ............................ 132/323 |
| 5,125,424 A | * | 6/1992 | Eisen | .......................... 132/323 |
| 5,261,430 A | * | 11/1993 | Mochel | ....................... 132/322 |
| 5,483,982 A | * | 1/1996 | Bennett et al. | .............. 132/323 |
| 5,538,023 A | | 7/1996 | Oczkowski et al. | |
| 5,692,531 A | | 12/1997 | Chodorow | |
| 5,829,458 A | | 11/1998 | Chodorow | |
| D497,222 S | * | 10/2004 | Ochs et al. | ................... D28/68 |
| 2003/0098037 A1 | | 5/2003 | Dougan et al. | |

FOREIGN PATENT DOCUMENTS

| | | |
|---|---|---|
| DE | 29 23 057 | 12/1980 |
| DE | 3831039 | 3/1990 |

* cited by examiner

*Primary Examiner*—Kevin Shaver
*Assistant Examiner*—Stephanie Willatt
(74) *Attorney, Agent, or Firm*—Egbert Law Offices

(57) ABSTRACT

A flosser apparatus has a handle with a first slot formed into a surface at a first end of the handle and a second slot formed into the surface adjacent the first end and extending in transverse relationship to the first slot, a locking member affixed to the handle, and a flosser element removably received in one of the first and second slots. The locking member retains the flosser element within one of the slots.

17 Claims, 3 Drawing Sheets

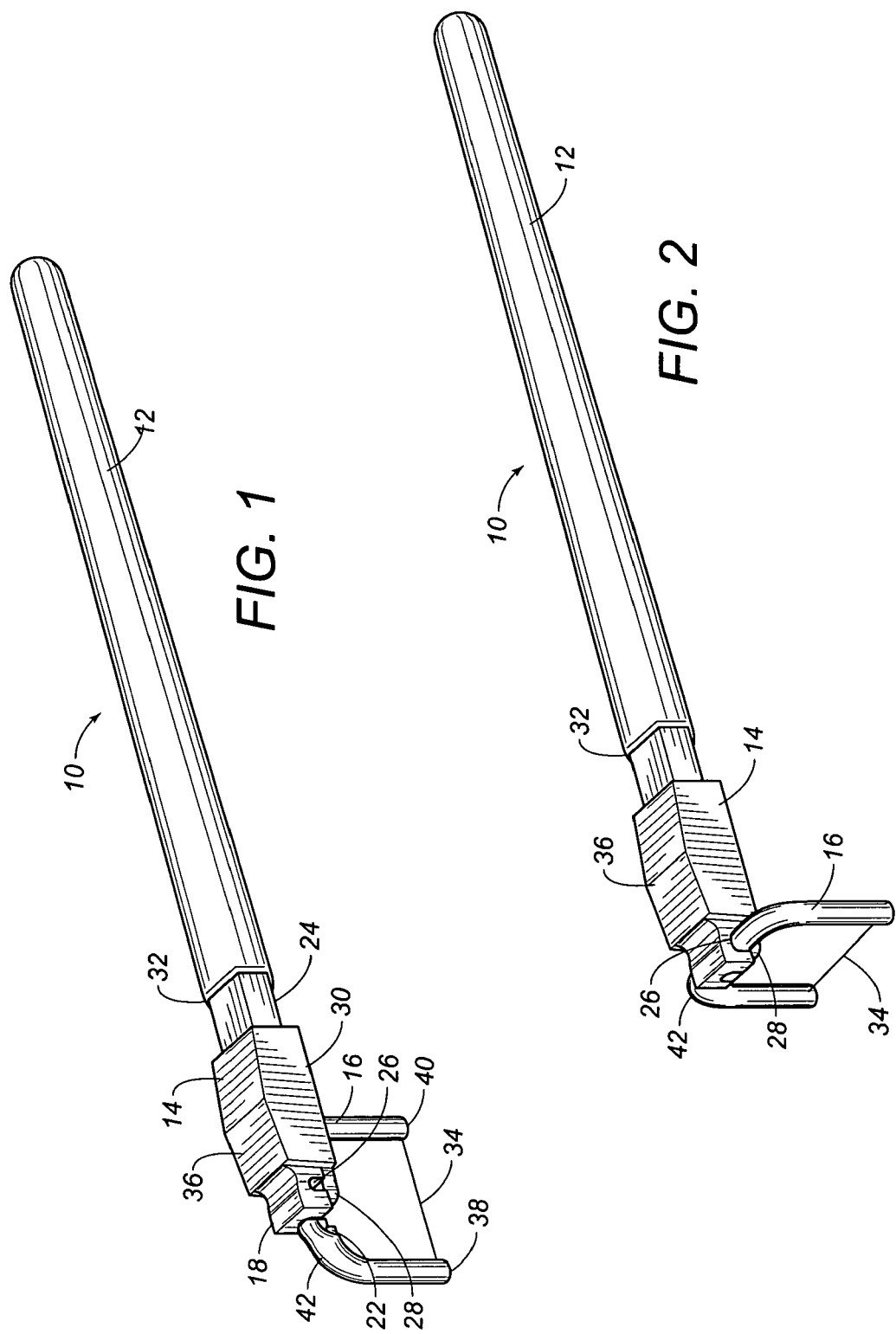

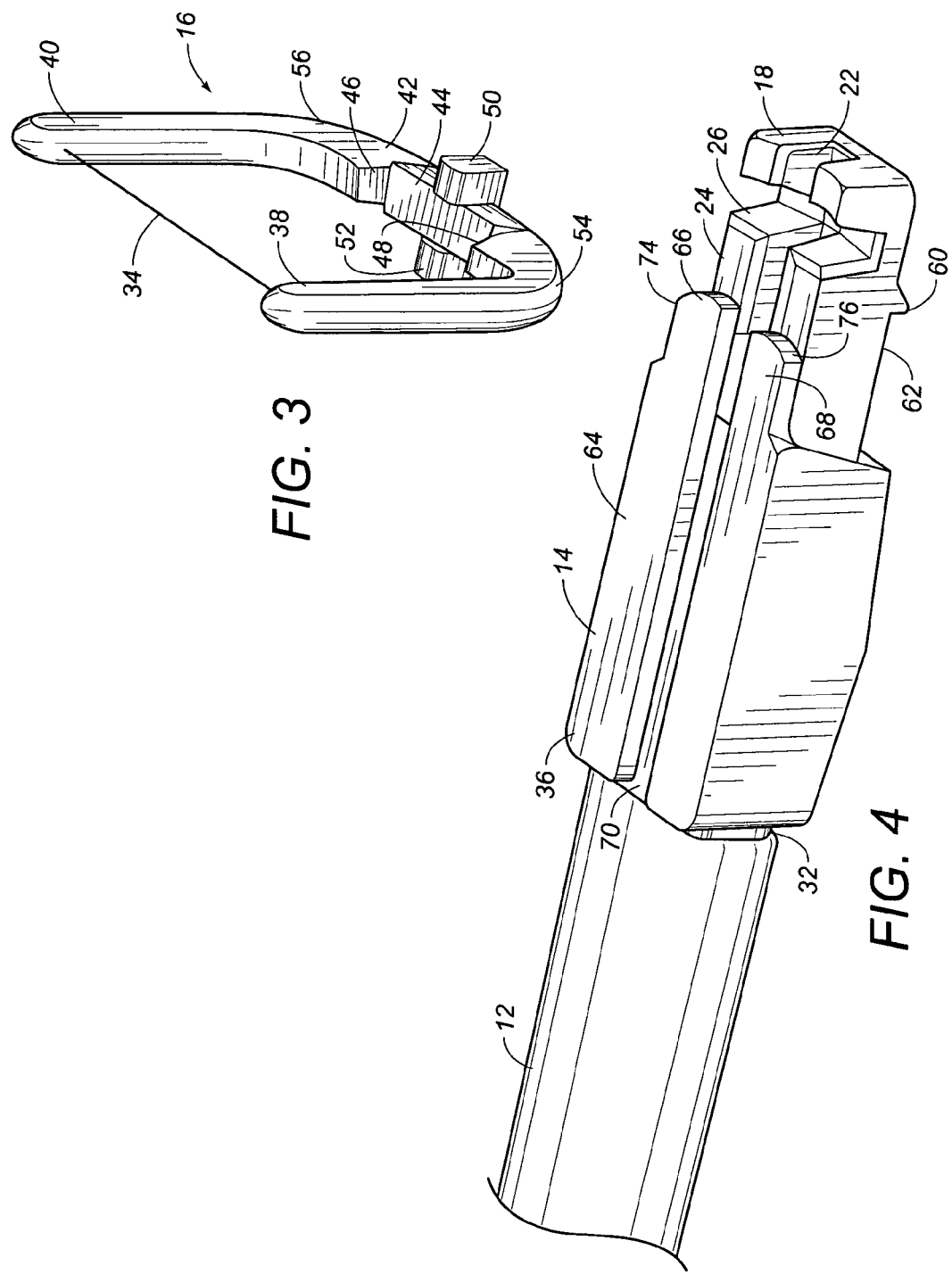

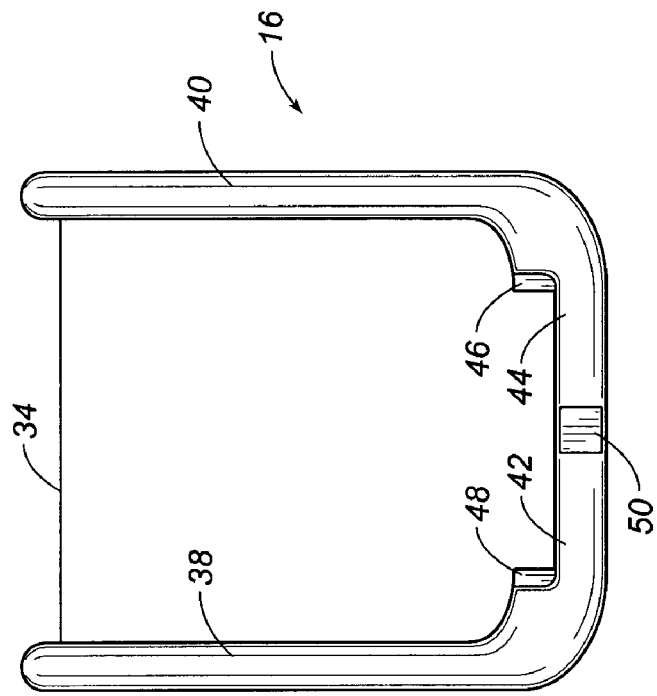
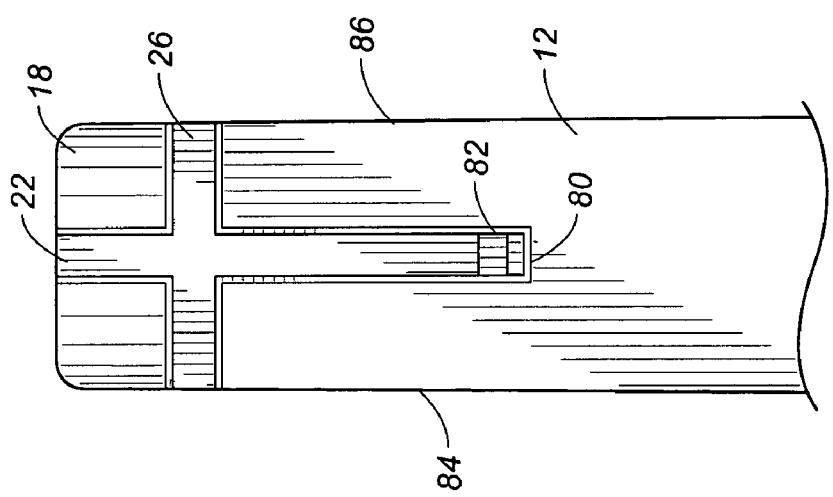

FLOSSER APPARATUS WITH DETACHABLE AND POSITIONABLE FLOSS ELEMENT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates to dental appliances. More particularly, the present invention relates to flosser apparatus where a small section of floss is secured between fixed arms supported on a shank. More particularly, the present invention relates to flosser apparatus having a detachable flosser element secured at an end of a handle.

BACKGROUND OF THE INVENTION

It has been well known in the past to provide some form of an implement to facilitate the removing of food particles from between a person's teeth. Such items have been frequently referred to as a toothpick and generally take the form of an elongated pointed tool which is adapted to be inserted between a person's teeth and moved in order to dislodge any food particles and plaque located between the teeth.

It has been further found to be desirable to not only employ the use of a pointed instrument, but also to employ the use or a strand of thread which is commonly referred to as dental floss. A segment from the dental floss is to be stretched taut and then inserted between the person's teeth and moved back and forth in order to effect removal of any lodged food particles and plaque.

Over time, various persons have discovered that it is practical and useful to apply a segment of a strand of dental floss into an implement that can be inserted into the mouth and manipulated so as to properly control the application of the floss. These devices are commonly known as "flossers". These devices provide a convenient mechanism for the flossing of teeth without the need for lengthy strands of floss. They also serve to more effectively reach into the spaces between the teeth so as to carry out flossing activities in a more effective manner.

In the past, various patents have issued relating to such flosser implements.

The earliest flosser apparatus that was revealed is in U.S. Pat. No. 2,187,899, issued on Jan. 23, 1940 to I. Henny. This patent describes a dental floss throw-away unit in which a single strand of thread extends between outwardly extending arms. A head is formed with the arms extending radially outwardly therefrom. The strand of floss extends in parallel relationship to the back of the head.

U.S. Pat. No. 2,648,341, issued on Aug. 11, 1953 to S. Moll teaches a dental floss holder which includes an elongated flexible member formed of plastic material. One end of the flexible member is rounded and provided with a transverse bore. A length of dental floss will extend through the transverse bore.

German Patent No. 29 23 057 teaches a dental floss applicator which includes a plurality of strands of floss which are far apart and extend in a plane which is perpendicular to the holder portion. Since the strands are not aligned with the shank portion of this flosser device, they are relatively difficult to apply as floss to one's teeth. The flosser is removably secured within a U-shaped head portion.

U.S. Pat. No. 4,280,518, issued on Jul. 28, 1981 to S. M. Gambaro teaches a tooth cleaning implement which includes an elongated member which has, at one end, a strand of dental floss tautly stretched thereacross. The opposite end of the elongated member is attached to a brush-like member which is used to facilitate the cleaning of teeth and dental bridges.

U.S. Design Pat. No. 276,088, issued on Oct. 23, 1984 to A. Fong describes a conventional flosser apparatus in which a single strand of floss is retained between a pair of arms extending outwardly of a head portion. A strand is connected to the head portion and extends so as to terminate at a pointed end.

U.S. Pat. No. 4,522,216, issued on Jun. 11, 1985, to R. L. Bunker describes a dental floss applicator which comprises a solid rectangular shaped body fitted with a pair of adjacent end arms forming a yolk arrangement in which the floss is drawn so as to form an X-shaped pattern. A small button fastener on each side of the applicator body permits the fastening of the floss after it has been stretched taut around the yolk.

German Patent No. 3,831,039 issued to H. Bauer describes a device for cleaning the narrow space between a bridge and the jaw. A pair of threads are connected to a guide. The threads are arranged in parallel to each other and are connected to each other by a number of parallel transverse threads.

U.S. Pat. No. 5,016,660, issued on May 21, 1991 to M. S. Boggs describes an automatic flossing tool having reciprocating tines supporting the flossing material and biased apart so as to assure proper tension on the flossing material. The device includes a means carried out by the tines for moving the flossing material between the tines and having a removable head so as to permit replacement of the head to provide sterile use for subsequent users.

In the recent past, it has been recognized that the above-identified flosser designs are often faulty because of the difficulty in placing the floss between the teeth and the difficulty associated with removing the floss from the teeth. In other circumstances, the close spacing of teeth will make it difficult to place the floss, in a slackened condition, between the teeth. Since the floss between the arms of the flosser apparatus of these prior designs is not in a very "tensioned" condition, then the floss can become frayed when placed in between and pulled out of the teeth. In order to overcome this problem, various U.S. patents have recently issued relating to the flosser apparatus with the ability to "tension" the strand prior to application and removal from the teeth. U.S. Pat. No. 5,538,023, issued on Jul. 23, 1996 to Oczkowski et al., describes a tensioning dental flosser having a holder, a bow and a length of dental floss spanning the bow. A movable element is provided which can cause a portion of the floss holder to move and tighten the strand of floss so as to reduce the slack in the floss. U.S. Pat. No. 5,692,531, issued on Dec. 2, 1997 to I. S. Chodorow, describes a dual strand dental flosser having a body part, first and second spaced apart arms extending from the body part, a first strand of dental floss extending axially between the arms and a second strand of dental floss extending axially between the arms and generally parallel to the first strand of dental floss. A lever mechanism extends from one of the arms which is movable so as to be moved toward the body part. When this lever is moved toward the body part, the first and second strands will tighten. U.S. Pat. No. 5,829,458, issued on Nov. 3, 1998 to I. S. Chodorow, describes a dental floss holder of similar construction to that of U.S. Pat. No. 5,692,531. It shows a variety of other mechanisms that can be used for tightening the dental floss.

There is a product on the market identified as the "GLIDE (™)" floss pick and manufactured by W. L. Gore and Associates, Inc. This is another type of flosser that includes a tensioning structure. In this device, the handles of the flosser can be squeezed together so as to cause the floss-holding arms to move away from each other about a pivot point spaced from the floss and between the floss and the pivot point.

One type of flosser apparatus is the subject of U.S. Patent Publication No. 2003/0098037 published on May 29, 2003 to Dougan et al. This flosser apparatus includes a handle and has a detachable flosser element located at one end of the handle. The handle has a top side and a bottom side. The top side at one end of the handle has a channel formed therein with tongue-and-groove elements extending into the channel. The bottom surface of the end of the handle is slightly curved and unchanneled. The flosser element has a pair of arms with a small length of floss fixedly secured thereto and extending therebetween. A strut serves to connect the two arms and is spaced in generally parallel relationship to the small section of floss. This strut includes a tongue-and-groove configuration which is mating received by the tongue-and-groove configuration of the slot on the top surface of the handle. When the strut of the flosser element is inserted into the channel on the top surface of the handle, the flosser apparatus is ready for use on teeth. After the use of the apparatus is completed, an upward force can be applied to the ends of the arms opposite the strut of the flosser element so as to cause the flosser element to separate from the channel formed on the top side to the handle.

Unfortunately, the flosser apparatus of U.S. Patent Publication No. 2003/0098037 presents certain problems to the users. First, it is somewhat difficult to release the flosser element from the channel on the top side of the handle. Secondly, the flosser element is positioned in only one direction in which the length floss extends transverse to the longitudinal axis of the handle. It is intented that the device be used in a manner of a toothbrush such that the handle will allow the user to reach the distant surfaces of the teeth. Unfortunately, the particular configuration of the floss extending transverse to the longitudinal axis of the handle makes the device somewhat difficult to use on the front teeth. Some difficult manipulations of the handle are required so that the floss is positioned in such a manner as to extend between the front teeth of the user. Additionally, the device provides no technique whereby the arms that are attached to the floss can be spread from each other so as to tighten the floss. A loose section of floss between the arms can present the problems described hereinbefore. Subsequent to use, the prior art device makes it difficult to release the used flosser element and insert a new flosser element into the channel. In many circumstances, contamination of hereto flosser element can result from a manual manipulation for installation.

It is an object of the present invention to provide a flosser apparatus in which the detachable flosser element can be positioned at different angles relatives to the handle.

It is another object of the present invention to provide a flosser apparatus whereby the detachable flosser element can be easily positioned and secured onto the handle.

It is a further object of the present invention to provide a flosser apparatus whereby the flosser element can be easily released from its receptacle on the handle.

It is a further object of the present invention to provide a flosser apparatus whereby the mechanism of locking the flosser element to the handle causes the arms associated with the flosser element to spread and tighten the floss extending between the arms.

It is a further object to the present invention to avoid contamination of the flosser element during installation and removal.

It is a further object of the present invention to provide a flosser apparatus which is easy to use, relatively inexpensive, and easy to manufacture and assemble.

These and other objects and advantages of the present invention will become apparent from a reading of the attached specification and appended claims.

BRIEF SUMMARY OF THE INVENTION

The present invention is a flosser apparatus having a handle, a locking member affixed to the handle, and a flosser element removably received on the handle. The handle has a first end and a second end. A first slot is formed into a surface of the handle adjacent to the first end. The handle also has a second slot formed into the surface of the handle adjacent to this first end. The first slot extends in transverse relationship to the second slot. The flosser element is removably received in one of the first and second slots. The locking member is manipulatable so as to retain the flosser element within the slot.

In the present invention, the first slot extends longitudinally along the handle. The second slot extends transversely to the first slot on the handle. The first slot has a curved portion at a side thereof opposite the first end of the handle. The first slot opens at this first end. The handle has a first side and a second side. The second slot has ends opening respectively at the first side and the second side of the handle.

In the present invention, the locking member is a body which is slidably affixed to the handle. This body is slidable between a first position away from the second slot and a second position adjacent to the second slot. The body of the locking member has a split extending entirely longitudinally therealong on one side of the body. The body has a first tongue extending outwardly on this side of the body and on one side of the split. The body of the locking member also has a second tongue extending outwardly therefrom on this side of the body and on a opposite side of the split. The first and second tongues are engaged with the flosser element when the locking element is in its second position. The first and second tongues are spaced from the flosser element when the locking member is in the first position.

The flosser element of the present invention has a generally U-shaped body with a first arm and a second arm and a strut extending therebetween. A length of floss is fixedly secured to the first arm and to the second arm so as to extend across the U-shaped body. The flosser element has a channel formed in the strut between the first and second arms. The flosser element also has finger members extending outwardly of sides of the strut and transverse relationship to the strut. The flosser element is positionable in a first position in the first and second slots of the handle such that the strut is received within the first slot and the finger members are received in the second slot. The flosser element is positionable in a second position such that the strut is received within the second slot and the finger members are received within the first slot. The flosser element also has a curved outer side extending on the surface between the first arm and the strut. The second arm also has a curved surface extending to an opposite end of the strut.

BRIEF DESCRIPTION OF THE SEVERAL VIEWS OF THE DRAWINGS

FIG. 1 is a perspective view of the flosser apparatus of the present invention showing the flosser element in a first position.

FIG. 2 is a perspective view of the flosser apparatus of the present invention showing the flosser element in a second position.

FIG. 3 is a perspective view showing the flosser element of the present invention.

FIG. 4 is a perspective close-up view of the slots at the end of the handle and the locking member positioned adjacent to the slots.

FIG. 5 is a plan view showing the slot configurations at the end of the handle.

FIG. 6 is a frontal view of the flosser element in accordance with the preferred embodiment of the present invention.

DETAILED DESCRIPTION OF THE INVENTION

Referring to FIG. 1, there is shown the flosser apparatus 10 in accordance with the teachings of the present invention. The flosser apparatus 10 includes a handle 12, a locking member 14, and a flosser element 16. The locking member 14 is affixed to the handle 12. The flosser element 16 is removably received in an end of the handle 12.

In the present invention, the handle 12 is an elongate member having a first end 18 and second end 20. The area adjacent to the second end 20 is a gripping area whereby the user can grasp the handle 12 by hand. The first end 18 includes a first slot 22 extending longitudinally along the bottom surface 24 of the handle 12. A second slot 26 is formed in the first end 18 of the handle 12 so as to extend transversely to the first slot 22 and transversely to the longitudinal axis of the handle 12.

The locking member 14 is positioned over the handle 12 adjacent to the end 18. The locking member 14 includes a tongue 28 extending outwardly therefrom on side 30 of the locking member 14. The locking member 14 is movable between a first position adjacent edge 32 and a second position (as shown in FIG. 1) in which the tongue 28 generally overlies the second slot 26. In this manner, the flosser element 16 is retained in the first slot 22 such that the length of floss 34 extends in longitudinally parallel alignment with the longitudinal axis of handle 12. When the locking member 14 has its body 36 retracted back to the edge 32, the tongue 28 will release from its position overlying the second slot 28 so that the flosser element 16 can be easily released, dropped or removed from the first slot 22.

The flosser element 16 includes a first arm 38, a second arm 30 and a strut 42. A portion of the strut 42 is received within the first slot 22. As will be described hereinafter, finger members extend outwardly respectively from sides of strut 42 such that the finger members are received within the second slot 26. When the tongue 28 overlies the second slot 26, the tongue 28 will serve to retain the finger members within the second slot 26 and, hence, retain the strut 42 within the first slot 22.

FIG. 2 shows that the flosser element 16 is arranged in a second position extending such that the length of floss 34 extends in transverse relationship to the longitudinal axis of the handle 12 of flosser apparatus 10. The strut 42 of flosser element 16 is illustrated as extending in the second slot 26. The tongue 28 of the body 36 of locking member 14 will overly the strut 42 so as to retain the strut 42 and the flosser element 16 in the desired position within second slot 26. When the body 36 of locking member 14 is retracted back to edge 32, the flosser element 16 can be easily released from the slot 26.

As can be seen in FIGS. 1 and 2, the flosser element 16 is positionable in either a direction aligned with the longitudinal axis of the handle 12 or a direction extending transverse to the longitudinal axis of the handle 12. As a result, the flosser element can be suitably positionable to the desires of the user. It is recommended that when the back teeth are being flossed, the flosser element 16 should assume the position shown in FIG. 2. When it is desired to floss the front teeth, then a more convenient position would be to place the flosser element 16 in the position illustrated in FIG. 1. Subsequent to use, finger pressure can be applied to the back surface of the body 36 of locking member 14 so as to retract the locking member 14 back to the position adjacent to edge 32. As a result, the flosser element 16 will be easily dropped from its position in one of the slots 22 or 26 without any direct manual contact with the flosser element 16. The arrangement of the tongue 28 associated with locking member 14, along with the cruciform configuration of the finger members and strut associated with the flosser element 16, causes the flosser element 16 to be rigidly supported within the respective slots 22 and 26. The flosser element 16 can be easily secured within the respective slots 22 and 26 by simply directing the end 18 of the flosser apparatus 10 to a supply of such flosser elements 16. When the strut 42 is positioned within the desired slot 22 or slot 26, the locking member 14 can be moved forwardly so that the flosser element 16 is retained in its desired position. As such, potentially contaminating contact with human fingers can be avoided. As will be described hereinafter, when the tongue 28 of the locking member 14 is moved forwardly, a force will be exerted onto the arms 38 and 40 of the flosser element 16 so as to spread the arms 38 and 40 away from each other and, hence, tighten the length of floss 34.

FIG. 3 illustrates the configuration of the flosser element 16. Flosser element 16 includes a first arm 38, a second arm 40 and a length of floss 34 extending therebetween. A strut 42 will extend between the arms 38 and 40 in generally parallel spaced relationship to the length of floss 34. Importantly, a channel 44 is formed in the surface of strut 42 facing the length of floss 34. Channel 44 has walls 46 and 48 extending upwardly therefrom toward the respective arms 40 and 38. Finger members 50 and 52 will extend transversely outwardly from the sides of the strut 42 generally in the center of the channel 44. The flosser element 16 includes a first curved outer side 54 extending from the strut 42 to the first arm 38. Another curved surface 56 will extend from the strut 42 to the second arm 40. The curved surfaces 54 and 56 facilitate the installation of the strut 42 within the respective slots. The flosser element 16 can be easily formed in an injection molding operation.

FIG. 4 is a detailed view showing the configuration of slots 22 and 26 as formed within the bottom surface 24 of handle 12. It can be seen that slot 22 extends generally longitudinally along the handle 12. The second slot 26 extends transversely to the first slot 22 adjacent to the end 18 of the handle 12. A stop 60 is formed on the top surface 62 of handle 12. The locking member 14 is illustrated in is first position generally adjacent to the edge 32 of the handle 12.

The locking member 14 can also be injection molded of a polymeric material. The locking member 14 has body 36 formed with a side 64. Side 64 has a first tongue 66 and a second tongue 68 extending outwardly therefrom. A split 70 is formed on the side 64 and extends entirely along the length of the locking member 14. The first tongue 66 extends outwardly on one side of the split 70. The second tongue 68 extends outwardly from side 64 on an opposite side of the split 70. The split 70 has an opening generally corresponding to the width of the slot 22. As a result, when the strut 42 of the flosser element 16 is inserted into the slot 22, the tongues 66 and 68 can move on opposite sides of the flosser element 16 so as to overlie the second slot 26. The tongues 66 and 68 have curved outer edges 74 and 76, respectively. These curved outer edges 74 and 76 will facilitate the contact with the side walls 46 and 48 of the channel 44 on strut 42 of flosser element 16. As a result, the tongues 66 and 68 will operate to spread the arms 38 and 40 away from each other and, hence, tighten the length of floss 34 extending therebetween.

In FIG. 4, it can be seen that the first slot 22 and the second slot 26 has a slightly widened opening adjacent to the surface 24. As a result, each of the slots 22 and 26 will serve to "funnel" the strut 42 of flosser element 16 thereinto. This further facilitates the introduction of the flosser element 16 into the respective slots 22 and 26.

FIG. 5 is a detailed view showing the configuration of the first slot 22 and the second slot 26 on the end 18 of handle 12. The first slot 22 has one end opening at end 18 of the handle 12. The opposite end of slot 22 extends for a distance longitudinally along the handle 12 so as to terminate at end 80. A curved surface 82 is formed at end 80 of slot 22. Curved surface 82 will generally match the curved outer surfaces 54 and 56 of the flosser element 16 so as to facilitate the introduction and removal of the flosser element 16 into the slot 22. The side walls of the slot 22 are illustrated as tapered so as to act as a funnel for the installation of the flosser element 16 thereinto. The second slot 26 extends transversely to the first slot 22. The second slot 26 has one end opening at side 84 of handle 12 and an opposite end opening at side 86 of handle 12. The second slot 26 is also illustrated as tapered so as to facilitate the installation of the flosser thereinto.

FIG. 6 is an end view showing the flosser element 16. Flosser element 16 is illustrated as having arms 38 and 40 extending upwardly from strut 42. Channel 44 is formed in the strut 42. Finger member 50 extends transversely outwardly from the strut 42. Importantly, the walls 46 and 48 are tapered. As a result, when the curved outer surfaces 74 and 76 of respective tongues 66 and 68 contact the side walls 46 and 48, a spreading action will be imparted to the associated arms 40 and 38 so as to cause the length of floss 34 to tighten.

The foregoing disclosure and description of the invention is illustrative and explanatory thereof. Various changes in the details of the construction can be made within the scope of the appended claims without departing from the true spirit of the invention. The present invention should only be limited by the following claims and their legal equivalents.

I claim:

1. A flosser apparatus comprising:
    a handle having a first end and a second end, said handle having a first slot formed into a surface thereof adjacent said first end, said handle having a second slot formed into said surface adjacent said first end, said first slot extending in transverse relationship to said second slot;
    a locking member affixed to said handle; and
    a flosser element removably received in one of said first and second slots, said locking member retaining said flosser element in the slot, said locking member comprising a body slidably affixed to said handle, said body slidable between a first position away from said second slot and a second position adjacent said second slot.

2. The apparatus of claim 1, said first slot extending longitudinally along said handle, and second slot extending transversely to said handle.

3. The apparatus of claim 1, said first slot having a curved portion at a side thereof opposite said first end, said first slot opening at said first end.

4. The apparatus of claim 1, said handle having a first side and a second side, said second slot having ends opening respectively at said first side and said second side.

5. The apparatus of claim 1, said body having a split extending entirely longitudinally therealong on one side of said body.

6. The apparatus of claim 5, said body having a first tongue extending outwardly therefrom on said one side of said body and on one side of said split, said body having a second tongue extending outwardly therefrom on said one side of said body and on an opposite side of said split.

7. The apparatus of claim 6, said first and second tongues being engaged with said flosser element when in said second portion, said first and second tongues being spaced from said flosser element when in said first position.

8. The apparatus of claim 1, said flosser element comprising:
    a generally U-shaped body having a first arm and a second arm and a strut extending therebetween; and
    a length of floss fixedly secured to said first arm and to said second arm and extending across said U-shaped body.

9. A flosser apparatus comprising:
    a handle having a first end and a second end, said handle having a first slot formed into a surface thereof adjacent said first end, said handle having a second slot formed into said surface adjacent said first end, said first slot extending in transverse relationship to said second slot;
    a locking member affixed to said handle; and
    a flosser element removably received in one of said first and second slots, said locking member retaining said flosser element in the slot, said flosser element comprising:
        a generally U-shaped body having a first arm and a second arm and a strut extending therebetween; and
        a length of floss fixedly secured to said first arm and to said second arm and extending across said U-shaped body, said flosser element having a channel formed in said strut between said first and second arms.

10. The apparatus of claim 9, said flosser element having finger members extending respectively outwardly from opposite sides of said strut and in transverse relation to said strut.

11. The apparatus of claim 10, said flosser element being positionable in a first position in said first and second slots of and handle such that said strut is received in said first slot and said finger members are received in said second slot, said flosser element being positionable in a second slot such that said strut is received in said second slot and said finger members are received in said first slot.

12. The apparatus of claim 9, said first arm having a curved outer surface extending to one end of said strut, said second arm having a curved outer surface extending to an opposite end of said strut.

13. A flosser apparatus comprising:
- a handle having a first end and a second end, said handle having a first slot formed into a surface thereof adjacent said first end;
- a locking member slidably affixed to said handle, said locking member having a tongue extending outwardly therefrom; and
- a flosser element removably received in said slot, said flosser element comprising:
  - a generally U-shaped body having a first arm and a second arm and a strut extending therebetween; and
  - a length of floss fixedly secured to said first arm and said second arm and extending across said U-shaped body, said locking member slidable between a first position in which said tongue is away from said strut and a second position in which said tongue overlies said strut.

14. The apparatus of claim 13, said strut having a channel formed therein, said tongue bearing against a side wall of said channel when in said second position so as to urge one of said first and second arms away from the other of said first and second arms.

15. The apparatus of claim 13, said handle having another slot extending transverse to said slot, said strut having a finger member extending outwardly transversely thereto, said finger member received in said another slot.

16. The apparatus of claim 13, said tongue of said locking member comprising a first tongue and a second tongue extending outwardly from a side of said locking member, said side of said locking member having a split formed therein and extending longitudinally therealong, said first tongue being on one side of said split, said second tongue being on an opposite side of said split.

17. A flosser apparatus comprising:
- a handle having a first end and a second end, said handle having a slot formed into a surface thereof and extending longitudinally therealong;
- a locking member slidably affixed to said handle, said locking member having a tongue extending outwardly therefrom; and
- a flosser element removably received in said slot, said flosser element comprising:
  - a generally U-shaped body having a first arm and a second arm and a strut extending therebetween; and
  - a length of floss fixedly secured to said first arm and said second arm and extending across said U-shaped body, said strut having a finger member extending outwardly of one side of said strut and in transverse relationship to said strut, said locking member slidable between a first position in which said tongue is away from said finger member and a second position in which said tongue overlies said finger member.

\* \* \* \* \*